(12) United States Patent
Tanaka et al.

(10) Patent No.: US 10,025,005 B2
(45) Date of Patent: Jul. 17, 2018

(54) COMPOSITION FOR OPTICAL MATERIALS

(71) Applicant: MITSUBISHI GAS CHEMICAL COMPANY, INC., Tokyo (JP)

(72) Inventors: Hiroaki Tanaka, Kanagawa (JP); Hiroshi Horikoshi, Chiba (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 447 days.

(21) Appl. No.: 14/373,739

(22) PCT Filed: Mar. 1, 2013

(86) PCT No.: PCT/JP2013/055619
§ 371 (c)(1),
(2) Date: Jul. 22, 2014

(87) PCT Pub. No.: WO2013/133144
PCT Pub. Date: Sep. 12, 2013

(65) Prior Publication Data
US 2015/0028270 A1 Jan. 29, 2015

(30) Foreign Application Priority Data
Mar. 5, 2012 (JP) ................................. 2012-047973

(51) Int. Cl.
| | |
|---|---|
| *G02B 5/02* | (2006.01) |
| *G02B 1/04* | (2006.01) |
| *C07D 331/02* | (2006.01) |
| *C08G 75/08* | (2006.01) |
| *C07D 409/14* | (2006.01) |

(52) U.S. Cl.
CPC .......... *G02B 1/041* (2013.01); *C07D 331/02* (2013.01); *C07D 409/14* (2013.01); *C08G 75/08* (2013.01); *G02B 1/04* (2013.01)

(58) Field of Classification Search
USPC ................. 523/102; 528/380, 403; 252/582; 524/418
See application file for complete search history.

(56) References Cited

U.S. PATENT DOCUMENTS

| | | | |
|---|---|---|---|
| 6,531,532 B1 * | 3/2003 | Yoshimura ............ | C08G 75/08 524/418 |
| 2004/0254258 A1 * | 12/2004 | Horikoshi ............. | C08G 75/08 523/102 |
| 2007/0149639 A1 | 6/2007 | Horikoshi et al. | |

FOREIGN PATENT DOCUMENTS

| | | |
|---|---|---|
| EP | 1369709 A2 | 12/2003 |
| JP | 09-110979 | 4/1997 |
| JP | 2001-002783 | 1/2001 |
| JP | 2001-002933 | 1/2001 |
| JP | 2004-43526 | 2/2004 |
| JP | 2004-137481 | 5/2004 |
| JP | 2004-269673 | 9/2004 |
| JP | 2004269673 * | 9/2004 |
| JP | 2005-336248 | 12/2005 |
| JP | 2006-348289 | 12/2006 |
| JP | 2009-242532 A | 10/2009 |
| JP | 2010-153296 | 7/2010 |
| JP | 2011-231185 * | 11/2011 |

OTHER PUBLICATIONS

Search report from International Search Report in PCT/JP2013/055619, dated Apr. 2, 2013.
Search Report issued by European patent office in Patent Application No. 13758146.8, dated Oct. 15, 2015.

* cited by examiner

*Primary Examiner* — Monique Peets
(74) *Attorney, Agent, or Firm* — Greenblum & Bernstein, P.L.C.

(57) ABSTRACT

The present invention inhibits the clouding of cured products obtained by polymerizing and curing a composition including sulfur and an episulfide compound, and inhibits clouding particularly in lenses, called plus-power lenses, that have large central thicknesses; and provides a composition for optical materials with which it is possible to predict and assess whether or not clouding will occur after curing and to determine quality at a stage before polymerization and curing. These objectives are achieved by, for example, a composition for optical materials that includes: sulfur, the turbidity value of which when made into a 30-mass % carbon disulfide solution is 10 ppm or less; and an episulfide compound. That is, clouding is prevented and excellent transparency is achieved in optical materials produced from said composition for optical materials that comprises an episulfide compound and sulfur that satisfies the aforementioned condition in terms of turbidity value.

8 Claims, No Drawings

COMPOSITION FOR OPTICAL MATERIALS

TECHNICAL FIELD

The present invention relates to a composition for optical materials, etc., and particularly relates to a composition for optical materials suitable for optical materials for a plastic lens, a prism, an optical fiber, an information recording substrate, a filter or the like, in particular for a plastic lens, and the like.

BACKGROUND ART

Plastic materials are lightweight, highly tough and easy to be dyed, and therefore are widely used recently for various types of optical materials, particularly eyeglass lenses. Optical materials, particularly eyeglass lenses, are specifically required to have, as physical properties, low specific gravity, high transparency and low yellowness, high heat resistance, high strength and the like, and as optical properties, high refractive index and high Abbe number. A high refractive index allows a lens to be thinner, and a high Abbe number reduces the chromatic aberration of a lens. However, as the refractive index is increased, the Abbe number is decreased. Therefore, it has been studied to improve both of the refractive index and the Abbe number. Among methods which have been proposed, the most representative method is a method using an episulfide compound as described in Patent Document 1.

Moreover, it has been studied to achieve a high refractive index, and a composition consisting of one or more types of inorganic compounds selected from inorganic compounds having a sulfur atom and/or a selenium atom and an episulfide compound described in Patent Document 2 has been proposed.

Furthermore, since white turbidity may occur when polymerizing and curing a composition comprising sulfur and an episulfide compound, proposals regarding the improvement of transparency have been made in Patent Documents 3-5.

However, in the case of lenses having a large central thicknesses called plus-power lenses, the occurrence of white turbidity was not successfully inhibited even by the above-described proposals. Since the plus-power lenses concentrate transmitted light, even slight reduction in transparency tends to be confirmed macroscopically, and it can be said that the form of the plus-power lenses tends to allow white turbidity to easily occur. Further, since compositions are used for optical materials, when white turbidity occurs after curing, all becomes defective products, resulting in heavy losses. Accordingly, a technique which makes it possible to predict whether or not white turbidity will occur after curing and to determine quality at a stage before curing has been desired.

PRIOR ART DOCUMENTS

Patent Documents

Patent Document 1: Japanese Laid-Open Patent Publication No. H09-110979
Patent Document 2: Japanese Laid-Open Patent Publication No. 2001-2783
Patent Document 3: Japanese Laid-Open Patent Publication No. 2004-43526
Patent Document 4: Japanese Laid-Open Patent Publication No. 2004-137481
Patent Document 5: Japanese Laid-Open Patent Publication No. 2004-269673

SUMMARY OF THE INVENTION

Problems to be Solved by the Invention

The problems to be solved by the present invention are to: inhibit white turbidity of cured products obtained by polymerizing and curing a composition including sulfur and an episulfide compound, in particular, inhibit the occurrence of white turbidity in lenses having a large central thicknesses called plus-power lenses; and provide a composition for optical materials with which it is possible to predict and assess whether or not white turbidity will occur after curing and to determine quality at a stage before polymerization and curing.

Means for Solving the Problems

The present inventors diligently made researches in view of the above-described circumstances, and the problems were solved by, for example, a composition for optical materials comprising: sulfur, the turbidity value of which when made into a 30% by mass solution of carbon disulfide is 10 ppm or less; and an episulfide compound. Thus the present invention was achieved.

Specifically, the present invention is as follows:

<1> A composition for optical materials, which comprises: sulfur, the turbidity value of which when made into a 30% by mass solution of carbon disulfide is 10 ppm or less; and an episulfide compound.
<2> The composition for optical materials according to item <1> above, further comprising a polythiol compound.
<3> The composition for optical materials according to item <1> above, wherein the sulfur has been preliminarily polymerized with the episulfide compound.
<4> The composition for optical materials according to item <1> above, wherein 10% by mass or more of the sulfur has been preliminarily polymerized with the episulfide compound.
<5> The composition for optical materials according to item <3> or <4> above, wherein the deaeration treatment is carried out after preliminarily polymerized.
<6> An optical material obtained by polymerizing the composition for optical materials according to any one of items <1> to <5> above.
<7> A method for producing a composition for optical materials, which comprises a step of preliminarily polymerizing sulfur, the turbidity value of which when made into a 30% by mass solution of carbon disulfide is 10 ppm or less, with an episulfide compound.
<8> The method for producing a composition for optical materials according to item <7> above, further having a step of adding a polythiol compound.
<9> The method for producing a composition for optical materials according to item <7> or <8> above, further having a step of carrying out the deaeration treatment.

Advantageous Effect of the Invention

According to the present invention, it is possible to inhibit white turbidity of cured products obtained by polymerizing and curing a composition including sulfur and an episulfide compound, in particular, to inhibit the occurrence of white turbidity in lenses having large central thicknesses, called plus-power lenses, which were difficult to be carried out by the prior art. Moreover, it is possible to provide a composition for optical materials with which it is possible to predict and assess whether or not white turbidity will occur after curing and to determine quality at a stage before polymerization and curing.

EMBODIMENTS FOR CARRYING OUT THE INVENTION

In the present invention, the turbidity is measured according to JIS K0101 using a turbidimeter with Kaolin standard solution as a standard. By carrying out the measurement, a sulfur, which has a turbidity value, when made into a 30% by mass solution of carbon disulfide, of 10 ppm or less, is used. The turbidity value is preferably 6 ppm or less, more preferably 3 ppm or less, and most preferably 2 ppm or less.

In the case where the turbidity value is more than 10 ppm, white turbidity often occurs after curing a composition when forming lenses having large central thicknesses called plus-power lenses. Accordingly, by measuring the turbidity value, it becomes possible to predict and assess whether or not white turbidity will occur after curing and to judge productivity at a stage before blending.

In the present invention, 9.0 g of sulfur is weighed and put into a vial container and then 21.0 g of carbon disulfide is added thereto, and a stirring bar is put into the mixture, which is stirred using a stirrer at room temperature for 30 minutes, thereby preparing a 30% by mass solution of carbon disulfide.

Examples of methods for producing sulfur include methods of sublimation and purification from natural sulfur ores, methods of mining underground sulfur by means of the melting method, and methods of recovery using, for example, hydrogen sulfide obtained in the process of desulfurization of petroleum oil, natural gas or the like, as a raw material, but any of these production methods may be employed to obtain the sulfur to be used in the present invention as long as the turbidity as a 30% by mass solution of carbon disulfide is 10 ppm or less. Preferably, a method of recovery using hydrogen sulfide obtained in the process of desulfurization as a raw material is employed. Further, commercially-available sulfurs are generally classified into finely-powdered sulfur, colloidal sulfur, precipitated sulfur, crystalline sulfur, sublimed sulfur and the like based on difference in forms and purification methods thereof, but the sulfur to be used in the preset invention may be a sulfur in any form or obtained by any purification method as long as the turbidity value obtained when made into a 30% by mass solution of carbon disulfide is 10 ppm or less. The sulfur is preferably a finely-powdered sulfur having fine particles, and more preferably a finely-powdered sulfur obtained by slowly cooling and solidifying melted sulfur and then powdering it. In view of the solubility, the particle size of the sulfur is preferably less than 10 mesh, more preferably less than 30 mesh, and most preferably less than 60 mesh.

The episulfide compound to be used in the present invention includes all episulfide compounds, and specific examples thereof are classified into a compound having a chain aliphatic skeleton, a compound having an aliphatic cyclic skeleton and a compound having an aromatic skeleton and listed below.

Examples of the compound having a chain aliphatic skeleton include a compound represented by the following formula (1):

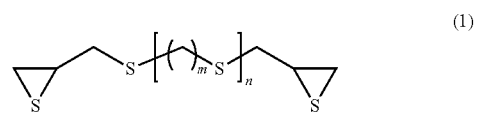

wherein m represents an integer from 0 to 4, and n represents an integer from 0 to 2.

Examples of the compound having an aliphatic cyclic skeleton include a compound represented by the following formula (2) or (3):

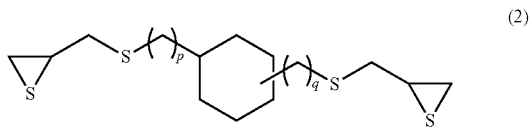

wherein p and q each independently represent an integer from 0 to 4;

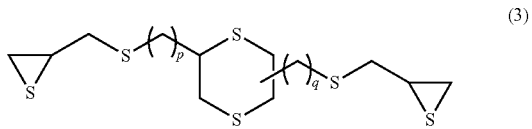

wherein p and q each independently represent an integer from 0 to 4.

Examples of the compound having an aromatic skeleton include a compound represented by the following formula (4):

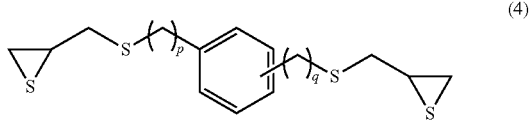

wherein p and q each independently represent an integer from 0 to 4.

Moreover, specific preferred examples of the compound represented by formula (1) above having a chain aliphatic skeleton include bis(β-epithiopropyl)sulfide, bis(β-epithiopropyl)disulfide, bis(β-epithiopropylthio)methane, 1,2-bis(β-epithiopropylthio)ethane, 1,3-bis(β-epithiopropylthio)propane, 1,4-bis(β-epithiopropylthio)butane and bis(β-epithiopropylthioethyl)sulfide.

Preferred examples of the episulfide compound having an aliphatic cyclic skeleton include 1,3- and 1,4-bis(β-epithiopropylthio)cyclohexane, 1,3- and 1,4-bis(β-epithiopropylthiomethyl)cyclohexane, 2,5-bis(β-epithiopropylthio)-1,4-dithiane and 2,6-bis(β-epithiopropylthioethylthiomethyl)-1,4-dithiane.

Preferred examples of the episulfide compound having an aromatic skeleton include 1,3- and 1,4-bis(β-epithiopropylthio)benzene and 1,3- and 1,4-bis(β-epithioproplythiomethyl)benzene.

Among them, the compound represented by formula (1) having a chain aliphatic skeleton is preferred, and specifically, bis(β-epoxypropyl)sulfide, bis(β-epoxypropyl)disulfide, bis(β-epoxypropylthio)methane, 1,2-bis(β-epoxypropylthio)ethane, 1,3-bis(β-epoxypropylthio)propane, 1,4-bis (β-epoxypropylthio)butane and bis(β-epoxypropylthioethyl) sulfide are preferred. Particularly preferred compounds are bis(β-epoxypropyl)sulfide (n=0 in formula (1)) and bis(β-epoxypropyl)disulfide (m=0 and n=0 in formula (1)), and bis(β-epoxypropyl)sulfide (n=0 in formula (1)) is the most preferred compound.

The amount of the sulfur to be used in the composition for optical materials of the present invention is usually 0.1 to 40 parts by mass, preferably 0.5 to 30 parts by mass, and particularly preferably 5 to 25 parts by mass, when the total amount of the sulfur and the episulfide compound is 100 parts by mass.

Preferably, in the composition for optical materials of the present invention, the sulfur has been preliminarily polymerized with the episulfide compound. Conditions for this preliminary polymerization reaction are preferably −10° C. to 120° C. and 0.1 to 240 hours, more preferably 0 to 100° C. and 0.1 to 120 hours, and particularly preferably 20 to 80° C. and 0.1 to 60 hours. It is effective to use a catalyst for promoting the preliminary reaction, and preferred examples thereof include 2-mercapto-1-methylimidazole, triphenylphosphine, 3,5-dimethylpyrazole, N-cyclohexyl-2-benzothiazolylsulfinamide, dipentamethylene thiuramtetrasulfide, tetrabutyl thiuram disulfide, tetraethyl thiuram disulfide, 1,2,3-triphenylguanidine, 1,3-diphenylguanidine, 1,1,3,3-tetramethyl eneguanidine, aminoguanidineurea, trimethyithiourea, tetraethylthiourea, dimethylethylthiourea, zinc dibutyldithiocarbamate, zinc dibenzyldithiocarbamate, zinc diethyldithiocarbamate, zinc dimethyldithiocarbamate and pipecorium pipecolyldithiocarbamate. Moreover, it is preferred that 10% by mass or more of the sulfur is consumed by this preliminary polymerization reaction (when the amount of the sulfur before the reaction is regarded as 100% by mass), and it is more preferred that 20% by mass or more of the sulfur is consumed thereby. The preliminary reaction may be performed in any atmosphere, for example, under inert gas such as air, nitrogen or the like, in a sealed state under normal pressure or raised or reduced pressure, or the like. In order to detect how much the preliminary reaction has proceeded, liquid chromatography or a refractometer can be used.

In the present invention, a polythiol compound can be added. The polythiol compound that can be used in the present invention includes all polythiol compounds, and specific examples thereof include methanedithiol, 1,2-dimercaptoethane, 2,2-dimercaptopropane, 1,3-dimercaptopropane, 1,2,3-trimercaptopropane, 1,4-dimercaptobutane, 1,6-dimercaptohexane, bis(2-mercaptoethyl)sulfide, 1,2-bis (2-mercaptoethylthio)ethane, 1,5-dimercapto-3-oxapentane, 1,8-dimercapto-3,6-dioxaoctane, 2,2-dimethylpropane-1,3-dithiol, 3,4-dimethoxybutane-1,2-dithiol, 2-mercaptomethyl-1,3-dimercaptopropane, 2-mercaptomethyl-1,4-dimercaptopropane, 2-(2-mercaptoethylthio)-1,3-dimercaptopropane, 1,2-bis(2-mercaptoethylthio)-3-mercaptopropane, 1,1,1-tris(mercaptomethyl)propane, tetrakis(mercaptomethyl)methane, 4,8-dimercaptomethyl-1, 11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, ethyleneglycolbis(2-mercaptoacetate), ethyleneglycolbis(3-mercaptopropionate), 1,4-butanediolbis(2-mercaptoacetate), 1,4-butanediolbis(3-mercaptopropionate), trimethylolpropanetris(2-mercaptoacetate), trimethylolpropanetris(3-mercaptopropionate), pentaerythritoltetrakis(2-mercaptoacetate), pentaerythritoltetrakis(3-mercaptopropionate), 1,1-dimercaptocyclohexane, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl) cyclohexane, 2,5-bis(mercaptomethyl)-1,4-dithiane, 2,5-bis (mercaptoethyl)-1,4-dithiane, 1,2-bis(mercaptomethyl) benzene, 1,3-bis(mercaptomethyl)benzene, 1,4-bis (mercaptomethyl)benzene, bis(4-mercaptophenyl)sulfide, bis(4-mercaptophenyl)ether, 2,2-bis(4-mercaptophenyl)propane, bis(4-mercaptomethylphenyl)sulfide, bis(4-mercaptomethylphenyl)ether and 2,2-bis(4-mercaptomethylphenyl) propane.

Among the above-described compounds, specific examples of preferred compounds include bis(2-mercaptoethyl)sulfide, pentaerythritoltetrakis(2-mercaptoacetate), pentaerythritoltetrakis(3-mercaptopropionate), 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1, 11-dimercapto-3,6,9-trithiaundecane, 1,1,3,3-tetrakis (mercaptomethylthio)propane, 1,3-bis(mercaptomethyl) benzene and 1,4-bis(mercaptomethyl)benzene. Specific examples of more preferred compounds include bis(2-mercaptoethyl)sulfide and 1,3-bis(mercaptomethyl)benzene.

When the total amount of the sulfur and the episulfide compound is 100 parts by mass, the amount of the polythiol compound to be used in the present invention is usually 1 to 30 parts by mass, preferably 2 to 20 parts by mass, and particularly preferably 3 to 15 parts by mass.

In the present invention, the composition for optical materials is preferably subjected to the deaeration treatment in advance. The deaeration treatment is carried out under reduced pressure before, during or after mixing a compound which can react with a part or all of the components of the composition, a polymerization catalyst and an additive. Preferably, the deaeration treatment is carried out under reduced pressure during or after mixing. The treatment conditions are as follows: under a reduced pressure of 0.001 to 50 torr; 1 minute to 24 hours; and 0° C. to 100° C. The degree of pressure reduction is preferably 0.005 to 25 torr, and more preferably 0.01 to 10 torr. The degree of pressure reduction may be varied within such a range. The deaeration time is preferably 5 minutes to 18 hours, and more preferably 10 minutes to 12 hours. The temperature at the time of deaeration is preferably 5 to 80° C., more preferably 10 to 60° C., and the temperature may be varied within these ranges. The operation of surface renewal of the composition for optical materials by means of stirring, blowing a gas, vibration caused by ultrasonic wave or the like during the deaeration treatment is preferable in terms of the enhancement of the deaeration effect. Components removed by the deaeration treatment are mainly dissolved gases such as hydrogen sulfide, low-boiling substances such as low-molecular-weight thiol, etc., but the type of components to be removed is not particularly limited as long as the effects of the present invention are exerted.

Hereinafter, a method for producing an optical material by polymerizing the composition for optical materials of the present invention will be described.

As a catalyst for polymerizing and curing the composition for optical materials of the present invention, an amine, an onium salt or a phosphine compound is used. Specific examples thereof include amines, quaternary ammonium salts, quaternary phosphonium salts, tertiary sulfonium salts, secondary iodonium salts and phosphine compounds. Among them, quaternary ammonium salts, quaternary phosphonium salts and phosphine compounds, which have good compatibility with the composition, are more preferred, and quaternary phosphonium salts are even more preferred. Specifically, more preferred examples of the compounds include quaternary ammonium salts such as tetra-n-butylammonium bromide, tetraphenylammonium bromide, triethylbenzyl ammonium chloride, cetyldimethylbenzyl ammonium chloride and 1-n-dodecyl pyridinium chloride, quaternary phosphonium salts such as tetra-n-butylphosphonium bromide and tetraphenyl phosphonium bromide and phosphine compounds such as triphenyl phosphine. Among them, triethylbenzyl ammonium chloride and tetra-n-butylphosphonium bromide are even more preferred compounds, and triethylbenzyl ammonium chloride is the most preferred compound. The polymerization catalysts may be used solely, or two or more of them may be used in combination.

The amount of the polymerization catalyst to be added cannot be determined categorically because it varies depending on the components of the composition, the mixing ratio and the method for polymerization/curing, but the amount is usually 0.001% by mass to 5% by mass, preferably 0.01% by mass to 1% by mass, and most preferably 0.01% by mass to 0.5% by mass of the total amount of the composition for optical materials. When the amount of the polymerization catalyst to be added is more than 5% by mass, the refractive index and the heat resistance of a cured product may be reduced and the product may be colored. When the amount of the polymerization catalyst to be added is less than 0.001% by mass, the composition may be insufficiently cured, resulting in insufficient heat resistance.

When polymerizing and curing the composition for optical materials, for the purpose of extension of the pot life, dispersion of heat generated by polymerization, etc., a polymerization modifier may be added according to need. Examples of the polymerization modifier include halides of groups 13 to 16 of the long form of the periodic table. Among them, halides of silicon, germanium, tin and antimony are preferred, and chlorides of germanium, tin and antimony, which have an alkyl group, are more preferred. Further, specifically, dibutyltin dichloride, butyltin trichloride, dioctyltin dichloride, octyltin trichloride, dibutyldichlorogermanium, butyltrichlorogermanium, diphenyldichlorogermanium, phenyltrichlorogermanium and triphenylantimony dichloride are even more preferred, and specifically, dibutyltin dichloride is the most preferred compound. These polymerization modifiers may be used solely, or two or more of them may be used in combination.

The amount of the polymerization modifier to be added is usually 0.0001 to 5.0% by mass, preferably 0.0005 to 3.0% by mass, and more preferably 0.001 to 2.0% by mass of the total amount of the composition for optical materials.

Further, at the time of obtaining an optical material by polymerizing and curing the composition for optical materials of the present invention, it is surely possible to add publicly-known additives such as an antioxidant, an ultraviolet absorber and a blueing agent to further improve practicability of the material obtained.

Preferred examples of the antioxidant include phenol derivatives. Among them, polyhydric phenols and halogen-substituted phenols are preferred compounds, and catechol, pyrogallol and alkyl-substituted catechols are more preferred compounds, and catechol and pyrogallol are the most preferred compounds. Preferred examples of the ultraviolet absorber include benzotriazole-based compounds, and specific examples of particularly preferred compounds include 2-(2-hydroxy-5-methylphenyl)-2H-benzotriazol, 5-chloro-2-(3,5-di-tert-butyl-2-hydroxyphenyl)-2H-benzotriazol, 2-(3-tert-butyl-2-hydroxy-5-methylphenyl)-5-chloro-2H-benzotriazole, 2-(3,5-di-tert-pentyl-2-hydroxyphenyl)-2H-benzotriazole, 2-(3,5-di-tert-butyl-2-hydroxyphenyl)-2H-benzotriazole, 2-(2-hydroxy-4-ethoxyphenyl)-2H-benzotriazole, 2-(2-hydroxy-4-butoxyphenyl)-2H-benzotriazole, 2-(2-hydroxy-4-octyloxyphenyl)-2H-benzotriazole and 2-(2-hydroxy-5-tert-octylphenyl)-2H-benzotriazole. Preferred examples of the blueing agent include anthraquinone-based compounds.

When the composition for optical materials of the present invention is easily released from the mold during polymerization, it is possible to use or add a publicly-known external and/or internal adhesiveness improving agent to control and improve the adhesiveness between a cured product obtained and the mold. Examples of the adhesiveness improving agent include publicly-known silane coupling agents and titanate compounds, and such substances may be used solely, or two or more of them may be used in combination. The amount of the adhesiveness improving agent to be added is usually 0.0001 to 5% by mass of the total amount of the composition for optical materials. Conversely, when the composition of the present invention is not easily released from the mold after polymerization, it is possible to use or add a publicly-known external and/or internal mold release agent to improve the ability of a cured product obtained to be released from the mold. Examples of the mold release agent include fluorine-based non-ionic surfactants, silicon-based non-ionic surfactants, phosphate esters, acidic phosphate esters, oxyalkylene-type acidic phosphate esters, alkali metal salts of acidic phosphate esters, alkali metal salts of oxyalkylene-type acidic phosphate esters, metal salts of higher fatty acid, higher fatty acid esters, paraffin, wax, higher aliphatic amides, higher aliphatic alcohols, polysiloxanes and aliphatic amine ethylene oxide adducts. These substances may be used solely, or two or more of them may be used in combination. The amount of the mold release agent to be added is usually 0.0001 to 5% by mass of the total amount of the composition for optical materials.

The method for producing an optical material by polymerizing and curing the composition for optical material of the present invention will be described in more detail below. All of the aforementioned respective components of the composition and additives such as antioxidant, ultraviolet absorber, polymerization catalyst, radical polymerization initiator, adhesiveness improving agent and mold release agent may be mixed together simultaneously in the same container with stirring. Alternatively, respective raw materials may be either mixed one by one in a stepwise manner, or first classified into several groups and mixed together under each group so that the mixtures of the respective groups are eventually mixed together in the same one container. Respective raw materials and auxiliary materials may be mixed in any order. The temperature to be set for mixing, the time required for mixing, etc. are basically not limited as long as respective components can be sufficiently mixed.

The composition for optical materials thus obtained may be subjected to filtration in order to prevent mixing of foreign substances, etc. and to improve the quality of lenses. The filtration is usually carried out using a filter having a pore diameter of 0.05 to 3 μm.

The composition for optical materials after the above-described reaction and treatment is injected into a mold made of glass or metal, and a polymerization and curing reaction is promoted by heating or irradiation with active energy ray such as ultraviolet light, and after that, and a product obtained is released from the mold. The optical material is produced in this way. The composition for optical materials is preferably polymerized and cured by heating to produce an optical material. In this case, the curing time is 0.1 to 200 hours, usually 1 to 100 hours, and the curing temperature is −10 to 160° C., usually −10 to 140° C. The polymerization may be conducted by carrying out a step of holding the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps. Further, in the method for producing the optical material of the present invention, it is preferred to anneal the cured product at a temperature of 50 to 150° C. for about 10 minutes to 5 hours after the completion of the polymerization in terms of eliminating distortion of the optical material. Moreover, a surface treatment such as dyeing, hard coating, impact-resistant coating, antireflection treatment and imparting anti-fog properties can be performed according to need.

EXAMPLES

Hereinafter, the present invention will be specifically described by way of working examples, but the present invention is not limited thereto. Evaluations were conducted in manners described below.

Turbidity of sulfur: the turbidity as a 30% by mass solution of carbon disulfide was measured using a turbidimeter (T-2600DA manufactured by Tokyo Denshoku Co., Ltd.). White turbidity of cured product: a cured product was irradiated with a fluorescent light in a dark room and the presence or absence of turbidity of the cured product was observed visually. The cured product was molded to prepare 10 lenses having a diameter of 75 mm and a lens power of +10 D. The case where no white turbidity was observed in the 10 lenses was rated as "A". The case where white turbidity was not observed in 9 lenses was rated as "B". The case where white turbidity was not observed in 7 or 8 lenses was rated as "C". The case where white turbidity was not observed in 6 lenses was rated as "D". The case where white turbidity was not observed in 5 lenses or less was rated as "E". A to D are regarded as acceptable.

Example 1

To 15 parts by mass of sulfur having a turbidity of 1.8 ppm, 85 parts by mass of bis(β-epithiopropyl)sulfide and 0.5 parts by mass of 2-mercapto-1-methylimidazole were added, and the mixture was preliminarily reacted at 60° C. until the consumption rate of sulfur became 50% (HPLC measurement by GPC mode). After that, the reaction mixture was cooled to 20° C., and then a mixed solution of 0.2 parts by mass of dibutyltin dichloride and 0.03 parts by mass of triethylbenzyl ammonium chloride as a polymerization catalyst was added thereto, and the mixture was homogeneously mixed and then deaerated under 10 Torr at 20° C. for 1 hour, filtered with a PTFE membrane filter having a pore diameter of 3.0 μm and injected into a mold for plus-power lenses. It was put into an oven for polymerization and curing with the temperature being elevated from 20° C. to 100° C. over 22 hours, and then demolded, thereby obtaining an optical material. The result is shown in Table 1.

Example 2

The same operation as that in Example 1 was carried out except that a sulfur having a turbidity of 2.7 ppm was used. The result is shown in Table 1.

Example 3

The same operation as that in Example 1 was carried out except that a sulfur having a turbidity of 5.6 ppm was used. The result is shown in Table 1.

Example 4

The same operation as that in Example 1 was carried out except that a sulfur having a turbidity of 10.0 ppm was used. The result is shown in Table 1.

Comparative Example 1

The same operation as that in Example 1 was carried out except that a sulfur having a turbidity of 12.3 ppm was used. The result is shown in Table 1.

TABLE 1

| Examples | Turbidity of sulfur (ppm) | White turbidity |
| --- | --- | --- |
| Example 1 | 1.8 | A |
| Example 2 | 2.7 | B |
| Example 3 | 5.6 | C |
| Example 4 | 10.0 | D |
| Comparative Example 1 | 12.3 | E |

Example 5

To 14 parts by mass of sulfur having a turbidity of 1.8 ppm, 79 parts by mass of bis(β-epithiopropyl)sulfide and 0.5 parts by mass of 2-mercapto-1-methylimidazole were added, and the mixture was preliminarily reacted at 60° C. until the consumption rate of sulfur became 50% (HPLC measurement by GPC mode). After that, the reaction mixture was cooled to 20° C., and then a mixed solution of 7 parts by mass of bis(2-mercaptoethyl)sulfide, 0.2 parts by mass of dibutyltin dichloride and 0.03 parts by mass of triethylbenzyl ammonium chloride as a polymerization catalyst was added thereto, and the mixture was homogeneously mixed and then deaerated under 10 Torr at 20° C. for 1 hour, filtered with a PTFE membrane filter having a pore diameter of 3.0 μm and injected into a mold for plus-power lenses. It was put into an oven for polymerization and curing with the temperature being elevated from 20° C. to 100° C. over 22 hours, and then demolded, thereby obtaining an optical material. The result is shown in Table 2.

Example 6

The same operation as that in Example 5 was carried out except that a sulfur having a turbidity of 2.7 ppm was used. The result is shown in Table 2.

Example 7

The same operation as that in Example 5 was carried out except that a sulfur having a turbidity of 5.6 ppm was used. The result is shown in Table 2.

Example 8

The same operation as that in Example 5 was carried out except that a sulfur having a turbidity of 10.0 ppm was used. The result is shown in Table 2.

Comparative Example 2

The same operation as that in Example 5 was carried out except that a sulfur having a turbidity of 12.3 ppm was used. The result is shown in Table 2.

TABLE 2

| Examples | Turbidity of sulfur (ppm) | White turbidity |
| --- | --- | --- |
| Example 5 | 1.8 | A |
| Example 6 | 2.7 | B |
| Example 7 | 5.6 | C |
| Example 8 | 10.0 | D |
| Comparative Example 2 | 12.3 | E |

Example 9

To 11 parts by mass of sulfur having a turbidity of 1.8 ppm, 79 parts by mass of 2,5-bis(β-epithiopropylthio)-1,4-dithiane, 0.2 parts by mass of 2-mercapto-1-methylimidazole and 5 parts by mass of bis(2-mercaptoethyl)sulfide were added, and the mixture was preliminarily reacted at 60° C. until the consumption rate of sulfur became 50% (HPLC measurement by GPC mode). After that, the reaction mixture was cooled to 20° C., and then a mixed solution of 5 parts by mass of 1,3-bis(mercaptomethyl)benzene, 0.2 parts by mass of dibutyltin dichloride and 0.03 parts by mass of triethylbenzyl ammonium chloride as a polymerization catalyst was added thereto, and the mixture was homogeneously mixed and then deaerated under 10 Torr at 20° C. for 1 hour, filtered with a PTFE membrane filter having a pore diameter of 3.0 μm and injected into a mold for plus-power lenses. It was put into an oven for polymerization and curing with the temperature being elevated from 20° C. to 100° C. over 22 hours, and then demolded, thereby obtaining an optical material. The result is shown in Table 3.

Example 10

The same operation as that in Example 9 was carried out except that a sulfur having a turbidity of 2.7 ppm was used. The result is shown in Table 3.

Example 11

The same operation as that in Example 9 was carried out except that a sulfur having a turbidity of 5.6 ppm was used. The result is shown in Table 3.

Example 12

The same operation as that in Example 9 was carried out except that a sulfur having a turbidity of 10.0 ppm was used. The result is shown in Table 3.

Comparative Example 3

The same operation as that in Example 9 was carried out except that a sulfur having a turbidity of 12.3 ppm was used. The result is shown in Table 3.

TABLE 3

| Examples | Turbidity of sulfur (ppm) | White turbidity |
| --- | --- | --- |
| Example 9 | 1.8 | A |
| Example 10 | 2.7 | B |
| Example 11 | 5.6 | C |
| Example 12 | 10.0 | D |
| Comparative Example 3 | 12.3 | E |

Example 13

To 14 parts by mass of sulfur having a turbidity of 1.8 ppm, 79 parts by mass of bis(β-epithiopropyl)sulfide, 0.2 parts by mass of 2-mercapto-1-methylimidazole and 2 parts by mass of 1,3-bis(mercaptomethyl)benzene were added, and the mixture was preliminarily reacted at 60° C. until the consumption rate of sulfur became 50% (HPLC measurement by GPC mode). After that, the reaction mixture was cooled to 20° C., and then a mixed solution of 5 parts by mass of 1,3-bis(mercaptomethyl)benzene, 0.2 parts by mass of dibutyltin dichloride and 0.03 parts by mass of triethylbenzyl ammonium chloride as a polymerization catalyst was added thereto, and the mixture was homogeneously mixed and then deaerated under 10 Torr at 20° C. for 1 hour, filtered with a PTFE membrane filter having a pore diameter of 3.0 μm and injected into a mold for plus-power lenses. It was put into an oven for polymerization and curing with the temperature being elevated from 20° C. to 100° C. over 22 hours, and then demolded, thereby obtaining an optical material. The result is shown in Table 4.

Example 14

The same operation as that in Example 13 was carried out except that a sulfur having a turbidity of 2.7 ppm was used. The result is shown in Table 4.

Example 15

The same operation as that in Example 13 was carried out except that a sulfur having a turbidity of 5.6 ppm was used. The result is shown in Table 4.

Example 16

The same operation as that in Example 13 was carried out except that a sulfur having a turbidity of 10.0 ppm was used. The result is shown in Table 4.

Comparative Example 4

The same operation as that in Example 13 was carried out except that a sulfur having a turbidity of 12.3 ppm was used. The result is shown in Table 4.

TABLE 4

| Examples | Turbidity of sulfur (ppm) | White turbidity |
| --- | --- | --- |
| Example 13 | 1.8 | A |
| Example 14 | 2.7 | B |
| Example 15 | 5.6 | C |
| Example 16 | 10.0 | D |
| Comparative Example 4 | 12.3 | E |

The invention claimed is:

1. A composition for optical materials, which comprises:
   sulfur, the turbidity value of which when made into a 30% by mass solution of carbon disulfide is 10 ppm or less; and
   an episulfide compound;
   wherein 10% by mass or more of the sulfur has been preliminarily polymerized with the episulfide compound by a catalyst for preliminary polymerization reaction selected from the group consisting of 2-mercapto-1-methylimidazole, triphenylphosphine, 3,5-dimethylpyrazole, N-cyclohexyl-2-benzothiazolylsulfinamide, dipentamethylene thiuramtetrasulfide, tetrabutyl thiuram disulfide, tetraethyl thiuram disulfide, 1,2,3-triphenylguanidine, 1,3-diphenylguanidine, 1,1,3,3-tetramethyleneguanidine, aminoguanidineurea, trimethylthiourea, tetraethylthiourea, dimethylethylthiourea, zinc dibutyldithiocarbamate, zinc dibenzyldithiocarbamate, zinc diethyldithiocarbamate, zinc dimethyldithiocarbamate and pipecorium pipecolyldithiocarbamate.

2. The composition for optical materials according to claim 1, further comprising a polythiol compound.

3. The composition for optical materials according to claim 1, wherein 20% by mass or more of the sulfur has been preliminarily polymerized with the episulfide compound.

4. The composition for optical materials according to claim 3, wherein a deaeration treatment is carried out after the preliminary polymerization.

5. An optical material obtained by polymerizing the composition for optical materials according to claim 1.

6. A method for producing a composition for optical materials, which comprises preliminarily polymerizing sulfur, the turbidity value of which when made into a 30% by mass solution of carbon disulfide is 10 ppm or less, with an episulfide compound by a catalyst for preliminary polymerization reaction selected from the group consisting of 2-mercapto-1-methylimidazole, triphenylphosphine, 3,5-dimethylpyrazole, N-cyclohexyl-2-benzothiazolylsulfinamide, dipentamethylene thiuramtetrasulfide, tetrabutyl thiuram disulfide, tetraethyl thiuram disulfide, 1,2,3-triphenylguanidine, 1,3-diphenylguanidine, 1,1,3,3-tetramethyleneguanidine, aminoguanidineurea, trimethylthiourea, tetraethylthiourea, dimethylethylthiourea, zinc dibutyldithiocarbamate, zinc dibenzyldithiocarbamate, zinc diethyldithiocarbamate, zinc dimethyldithiocarbamate and pipecorium pipecolyldithiocarbamate.

7. The method for producing a composition for optical materials according to claim 6, further comprising adding a polythiol compound.

8. The method for producing a composition for optical materials according to claim 6, further comprising carrying out a deaeration treatment.

* * * * *